(12) United States Patent
Sohn et al.

(10) Patent No.: US 10,286,131 B2
(45) Date of Patent: May 14, 2019

(54) PUMP FOR RIGHT ATRIUM

(71) Applicant: RAINBOW MEDICAL LTD, Herzeliya (IL)

(72) Inventors: Zev Sohn, Karnei Shomron (IL); Yossi Gross, Moshav Mazor (IL)

(73) Assignee: RAINBOW MEDICAL LTD., Herzliya (IL)

( * ) Notice: Subject to any disclaimer, the term of this patent is extended or adjusted under 35 U.S.C. 154(b) by 109 days.

(21) Appl. No.: 15/543,789

(22) PCT Filed: Jan. 14, 2016

(86) PCT No.: PCT/IL2016/050050
§ 371 (c)(1),
(2) Date: Jul. 14, 2017

(87) PCT Pub. No.: WO2016/113743
PCT Pub. Date: Jul. 21, 2016

(65) Prior Publication Data
US 2018/0001004 A1    Jan. 4, 2018

Related U.S. Application Data

(60) Provisional application No. 62/103,937, filed on Jan. 15, 2015.

(51) Int. Cl.
*A61M 1/12*    (2006.01)
*A61M 1/10*    (2006.01)

(52) U.S. Cl.
CPC ........ *A61M 1/1003* (2014.02); *A61M 1/1008* (2014.02); *A61M 1/1046* (2013.01);
(Continued)

(58) Field of Classification Search
CPC .... A61M 1/10; A61M 1/1003; A61M 1/1008; A61M 1/1037; A61M 1/1046; A61M 1/1048; A61M 1/106; A61M 1/12; A61M 1/122
See application file for complete search history.

(56) References Cited

U.S. PATENT DOCUMENTS 6,406,422 B1    6/2002  Landesberg
2002/0173742 A1* 11/2002  Keren .............. A61B 17/00234
                                                                    604/9
(Continued)

FOREIGN PATENT DOCUMENTS

WO    2007/149562    12/2007
WO    2010/128501    11/2010
WO    2016/113743     7/2016

OTHER PUBLICATIONS

An International Search Report and a Written Opinion both dated Apr. 15, 2016, which issued during the prosecution of Applicant's PCT/IL2016/050050.
(Continued)

*Primary Examiner* — Allen Porter
(74) *Attorney, Agent, or Firm* — Sughrue Mion, PLLC (57) ABSTRACT

Apparatus and methods are described, including apparatus (20) for implanting in a heart of a human subject. The apparatus includes an interatrial anchor (22) shaped to define an opening (26) having a diameter of 4-8 mm, and a bag (24) in fluid communication with the opening of the anchor. The apparatus is shaped to fit within a right atrium of the heart of the subject, and has a capacity of between 4 and 20 cm3. Other applications are also described.

14 Claims, 6 Drawing Sheets

(52) U.S. Cl.
CPC .......... *A61M 1/1072* (2013.01); *A61M 1/122* (2014.02); *A61M 1/125* (2014.02); *A61M 1/106* (2013.01); *A61M 1/1037* (2013.01); *A61M 1/127* (2013.01)

(56) References Cited

U.S. PATENT DOCUMENTS

| | | | |
|---|---|---|---|
| 2005/0148925 A1 | 7/2005 | Rottenberg et al. | |
| 2005/0154250 A1* | 7/2005 | Aboul-Hosn | A61M 1/3621 600/16 |
| 2005/0165344 A1* | 7/2005 | Dobak, III | A61F 2/01 604/8 |
| 2008/0004485 A1* | 1/2008 | Moreschi | A61M 1/1075 600/16 |
| 2008/0207986 A1* | 8/2008 | Choy | A61M 1/122 600/16 |
| 2010/0057192 A1* | 3/2010 | Celermajer | A61B 17/0057 623/1.26 |
| 2011/0218480 A1 | 9/2011 | Rottenberg et al. | |
| 2011/0306916 A1* | 12/2011 | Nitzan | A61F 2/2418 604/9 |
| 2012/0059213 A1* | 3/2012 | Spence | A61M 1/3653 600/16 |
| 2014/0213959 A1 | 7/2014 | Nitzan et al. | |
| 2015/0335801 A1* | 11/2015 | Farnan | A61M 1/1008 600/16 |
| 2016/0166747 A1* | 6/2016 | Frazier | A61M 1/122 600/16 |

OTHER PUBLICATIONS

U.S. Appl. No. 62/103,937, filed Jan. 15, 2015.

\* cited by examiner

PUMP FOR RIGHT ATRIUM

CROSS-REFERENCE TO RELATED APPLICATIONS

The present application is the US national stage application of PCT IL/2016/050050, filed Jan. 14, 2016, which published as PCT Publication WO 2016/113743 to Sohn, et al., and which claims priority from U.S. Provisional Application No. 62/103,937 to Sohn, filed Jan. 15, 2015, entitled "Pump For Right Atrium," which is incorporated herein by reference.

FIELD OF THE INVENTION

The present invention relates to treatment of left-side heart failure.

BACKGROUND

Left-side heart failure is a life-threatening condition in which the left side of the heart is unable to pump enough blood to the body. Symptoms of left-side heart failure include pulmonary edema, which results from increased congestion in the pulmonary vasculature.

SUMMARY OF EMBODIMENTS

In some applications of the present invention, apparatus is inserted into the right atrium of a subject, the apparatus including an interatrial anchor and a bag in fluid communication with an opening of the anchor. The anchor is anchored to the interatrial septum of the subject, such that the anchor provides fluid communication between the left atrium of the subject and the bag. During atrial diastole, blood is received from the left atrium into the bag. The flow of blood from the left atrium reduces the pressure in the left atrium, which helps to relieve symptoms of left-side heart failure, e.g., by reducing congestion in the pulmonary vasculature. Then, during atrial systole, musculature of the right atrium is used to pump blood from the bag into the left atrium, by compressing the bag. The pumping of the blood from the bag supplements the pumping of the left atrium, by providing additional "atrial kick". Furthermore, by occupying a portion of the right atrium, and by "diverting" some of the energy provided by muscles of the right atrium to compression of the bag, the bag reduces the volume of blood that leaves the right atrium, thus further helping to reduce congestion in the pulmonary vasculature.

There is therefore provided, in accordance with some applications of the present invention, apparatus for implanting in a heart of a human subject, the apparatus including:
an interatrial anchor shaped to define an opening having a diameter of 4-8 mm; and
a bag in fluid communication with the opening of the anchor,
the apparatus being shaped to fit within a right atrium of the heart of the subject and having a capacity of between 4 and 20 cm3.

In some applications, a greatest length of the apparatus is between 4 and 15 cm.

In some applications, the greatest length of the apparatus is between 4 and 10 cm.

In some applications, the apparatus further includes a shunt disposed between the anchor and the bag.

In some applications, the capacity of the apparatus is between 8 and 20 cm3.

In some applications, the capacity of the apparatus is between 8 and 16 cm3.

In some applications, the bag is inelastic.

In some applications, the bag is capable of withstanding an internal pressure of 200 mmHg without stretching.

In some applications, the apparatus further includes a bag anchor configured to anchor the bag to the right atrium of the subject.

In some applications, the bag anchor is configured to anchor the bag to a right atrial appendage of the subject.

In some applications, the bag anchor includes an element selected from the group consisting of: a barb, a hook, and a screw.

In some applications, the bag anchor includes a structure configured to span the right atrium from a right atrial appendage of the right atrium to an opposite side of the right atrium from the right atrial appendage.

In some applications, the structure is shaped to define a loop that is configured to loop around an inferior vena cava of the subject in a vicinity of a junction between the inferior vena cava and the subject's right atrium.

In some applications, the structure is shaped to define an elongate section having a length that is between 4 cm and 14 cm.

In some applications, the bag anchor is configured to anchor the bag to the right atrium of the subject by pushing the bag toward an outer wall of the right atrium at the right atrial appendage.

In some applications, an outer surface of the bag is rough.

In some applications, the outer surface of the bag is woven.

In some applications, an outer surface of the bag is porous.

In some applications, the outer surface of the bag is shaped to define a plurality of laser-drilled pores.

In some applications, a portion of the bag is shaped to snugly fit into a right atrial appendage of the subject, at least when the bag is fully expanded.

In some applications, a surface of the bag, when the bag is fully expanded, is generally tear-shaped.

In some applications, the diameter of the opening is 5-7 mm.

There is further provided, in accordance with some applications of the present invention, a method for treating a subject, the method including:
during atrial diastole of the subject, receiving blood from the left atrium of the subject into a bag that is disposed within a right atrium of the subject; and
during atrial systole of the subject, utilizing musculature of the right atrium to pump blood from the bag into the left atrium, by compressing the bag.

In some applications, utilizing musculature of the right atrium includes utilizing musculature of a right atrial appendage of the subject.

In some applications, compressing the bag includes compressing the bag while the bag is at least partly inside of a right atrial appendage of the subject.

In some applications, utilizing the musculature of the right atrium to pump the blood from the bag includes utilizing the musculature of the right atrium to pump between two and eight cm3 of blood from the bag.

In some applications, utilizing the musculature of the right atrium to pump the blood from the bag includes utilizing the musculature of the right atrium to pump between three and five cm3 of blood from the bag.

There is further provided, in accordance with some applications of the present invention, a method including:

inserting apparatus into a right atrium of a subject, the apparatus including an interatrial anchor and a bag in fluid communication with an opening of the anchor; and anchoring the anchor to an interatrial septum of the subject, such that the anchor provides fluid communication between a left atrium of the subject and the bag.

In some applications, the method further includes placing the bag in a right atrial appendage of the subject.

In some applications, the method further includes using a bag anchor to anchor the bag to the right atrium of the subject.

In some applications, anchoring the bag to the right atrium of the subject includes anchoring the bag to a right atrial appendage of the subject.

In some applications, the method further includes inducing fibrosis to anchor the bag to the right atrial appendage of the subject.

In some applications, anchoring the bag to the right atrium of the subject includes placing a structure in the right atrium that spans the right atrium from a right atrial appendage of the right atrium to an opposite side of the right atrium from the right atrial appendage.

In some applications, placing the structure in the right atrium includes placing a loop of the structure within the right atrium such that the loop loops around an inferior vena cava of the subject in a vicinity of a junction between the inferior vena cava and the subject's right atrium.

In some applications, placing the structure in the right atrium includes placing the structure in the right atrium, the structure defining an elongate section having a length that is between 4 cm and 14 cm.

In some applications, anchoring the bag to the right atrium of the subject includes pushing the bag toward an outer wall of the right atrium at the right atrial appendage, by placing the structure in the right atrium.

The present invention will be more fully understood from the following detailed description of applications thereof, taken together with the drawings, in which:

DETAILED DESCRIPTION OF EMBODIMENTS

Figure 1:
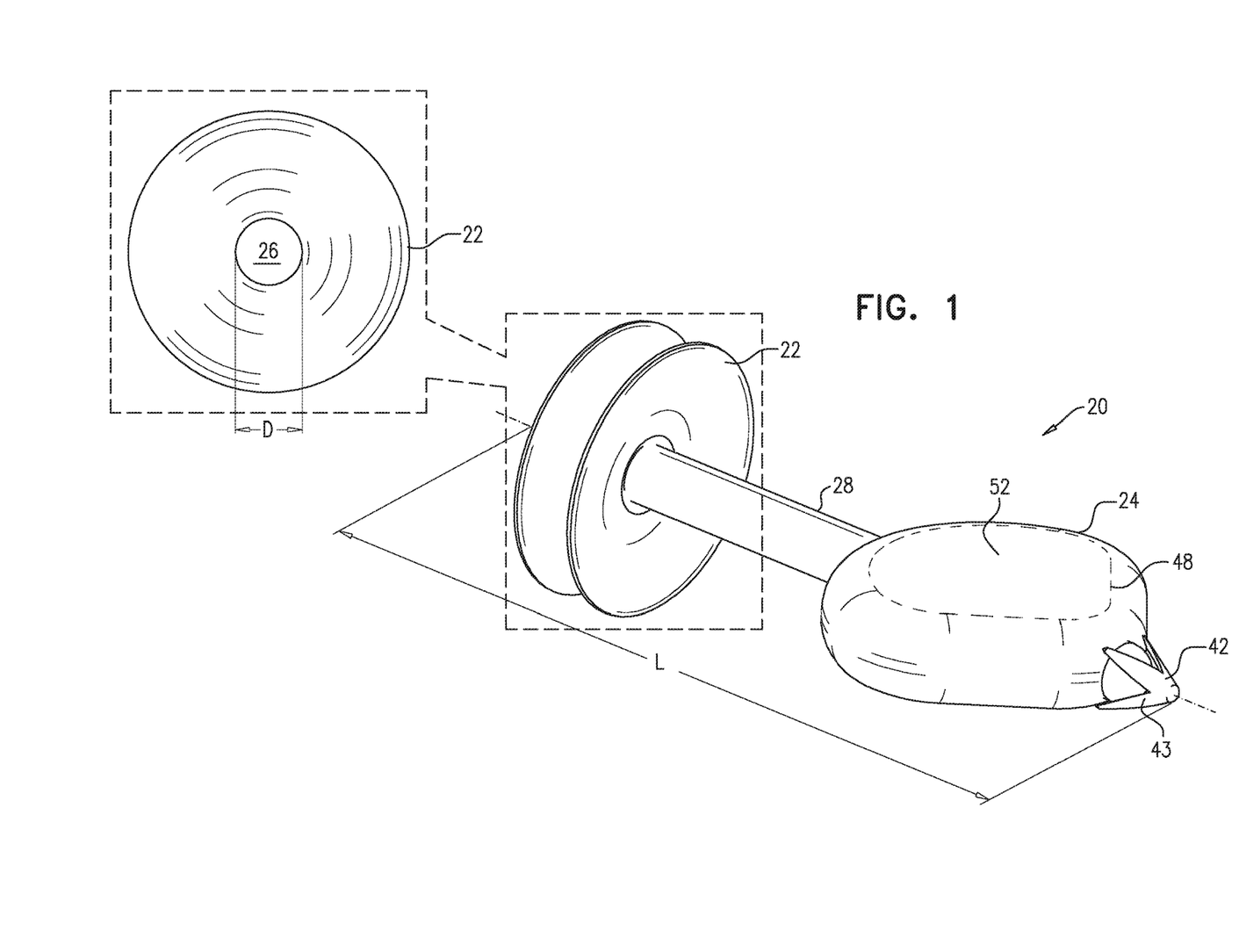
FIG. 1 is a schematic illustration of apparatus for implanting in a heart of a human subject, in accordance with some applications of the present invention.

Reference is made to FIG. 1, which is a schematic illustration of apparatus 20 for implanting in a heart of a human subject, in accordance with some applications of the present invention. Apparatus 20 comprises an interatrial anchor 22, and a bag 24 in fluid communication with the opening 26 of anchor 22. In some applications, apparatus 20 further comprises a shunt 28 disposed between the anchor and the bag. Typically, the capacity of the apparatus (e.g., the capacity of the bag, or the combined capacity of the bag and the shunt) is at least 4 cm3 and/or less than 20 cm3, e.g., 8-20 cm3, e.g., 8-16 cm3.

Apparatus 20 is shaped to fit within the right atrium of the heart of the subject; for example, a greatest length L of the apparatus may be greater than 4 cm and/or less than 15 cm, e.g., between 4 and 10 cm. (It is noted that, in order to conform to the geometry of the right atrium, apparatus 20 is typically not as straight as is shown; rather, bag 24 and/or shunt 28 typically turns, such that opening 26 is not aligned with the opposite end of the apparatus. In such applications, length L is the length while moving along the apparatus, i.e., the distance that an ant would need to travel to move from one end of the apparatus to the other end.) Opening 26 typically has a diameter D of at least 4 mm and/or less than 8 mm, e.g., 5-7 mm. Typically, the bag is inelastic, and/or is capable of withstanding an internal pressure of 200 mmHg without stretching. The bag may be made from any biocompatible material, and/or from materials used in heart valves, e.g., pericardial tissue.

Typically, a portion of the bag is shaped to snugly fit into the right atrial appendage of the subject, at least when the bag is fully expanded. For example, a surface 52 of the bag, when the bag is fully expanded or fully flattened, may be generally tear-shaped, the tear shape facilitating the snug fitting of the bag in the right atrial appendage. A tear-shaped outline of the perimeter of surface 52 is shown in FIG. 1. Portion 48 of the outline, which is the "top" of the tear, may be generally straight-lined, as shown in FIG. 1. Alternatively, portion 48 may be somewhat concave or convex. In some applications, portion 48 is generally straight-lined when the bag is less than fully expanded, and becomes more convex as the bag is expanded.

In some applications, apparatus 20 further comprises a bag anchor 42 configured to anchor the bag to the right atrium (e.g., the right atrial appendage) of the subject, as described hereinbelow with reference to FIG. 2B. Bag anchor 42 typically comprises a barb, a hook, and/or a screw. For example, FIG. 1 shows a bag anchor that comprises a plurality of barbs 43.

Figure 2A:
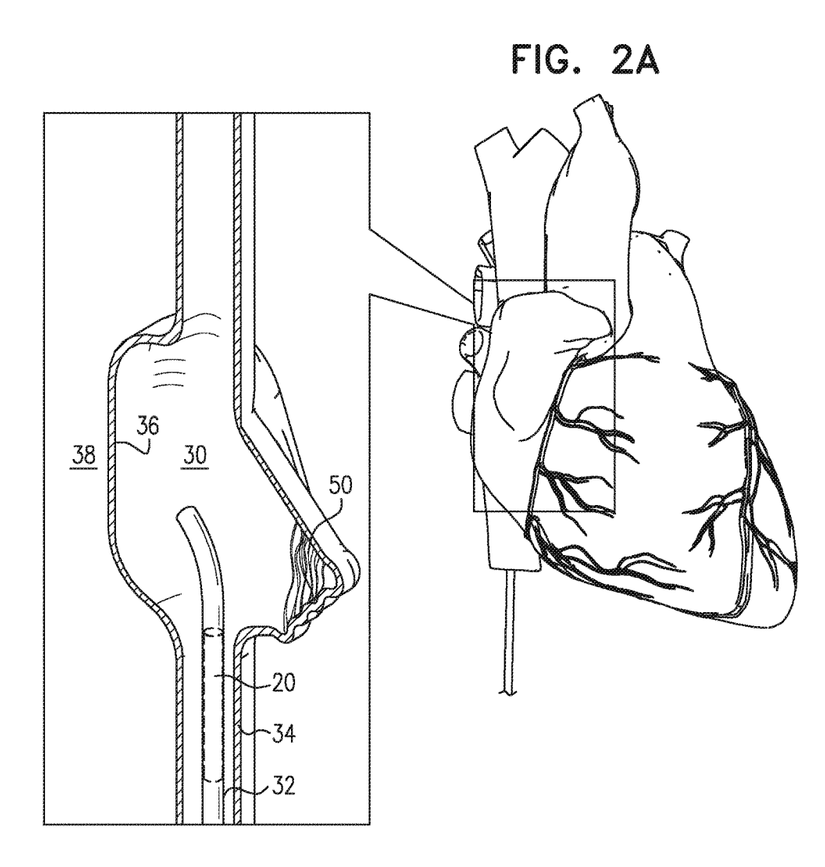
FIGS. 2A-B are schematic illustrations of a method for implanting apparatus in a right atrium of a subject, in accordance with some applications of the present invention.
Figure 2B:
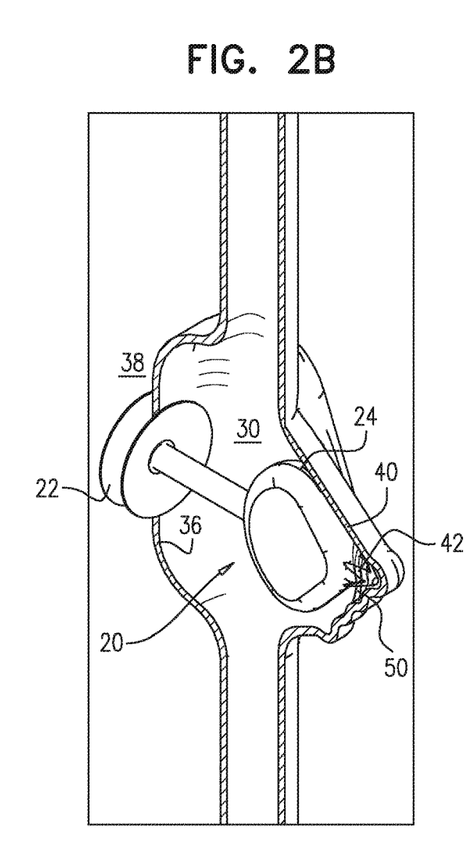

Reference is now made to FIGS. 2A-B, which are schematic illustrations of a method for implanting apparatus 20 in a right atrium 30 of a subject, in accordance with some applications of the present invention. FIG. 2A shows apparatus 20 being inserted into right atrium 30, e.g., via a catheter 32 that is passed through the vena cava 34. Following the insertion of apparatus 20, the interatrial septum 36 of the subject is punctured, and anchor 22 is subsequently anchored to interatrial septum 36, as shown in FIG. 2B, such that the anchor provides fluid communication between the left atrium 38 and bag 24. Bag 24 is typically placed in the right atrial appendage 40 of the subject. In some applications, bag anchor 42 is used to anchor the bag to the right atrium (e.g., to right atrial appendage 40); for example, the bag anchor may anchor the bag to pectinate muscles 50 in the right atrial appendage.

Figure 3A:
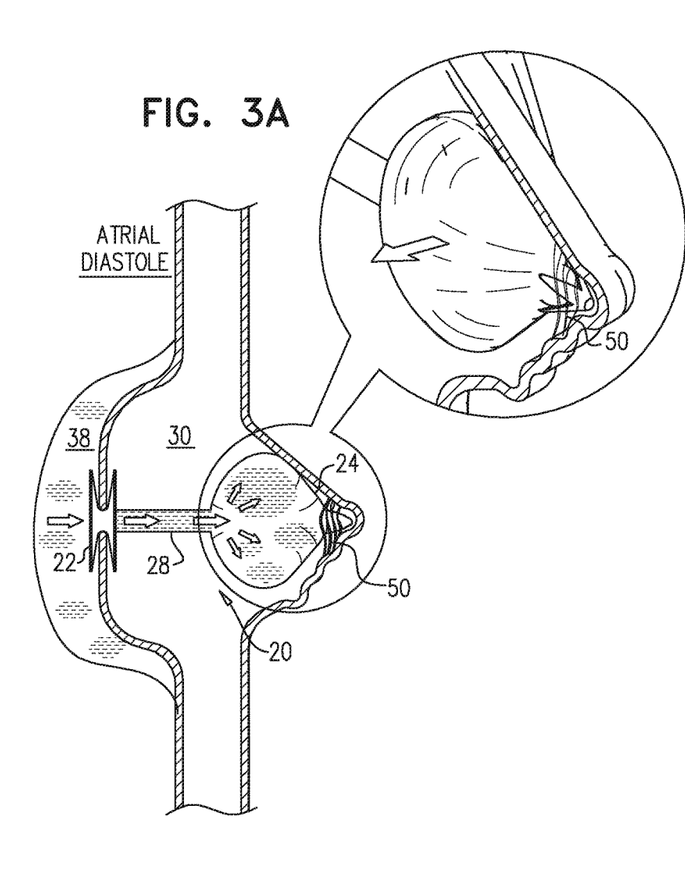
FIGS. 3A-B show the operation of apparatus, in accordance with some applications of the present invention.
Figure 3B:
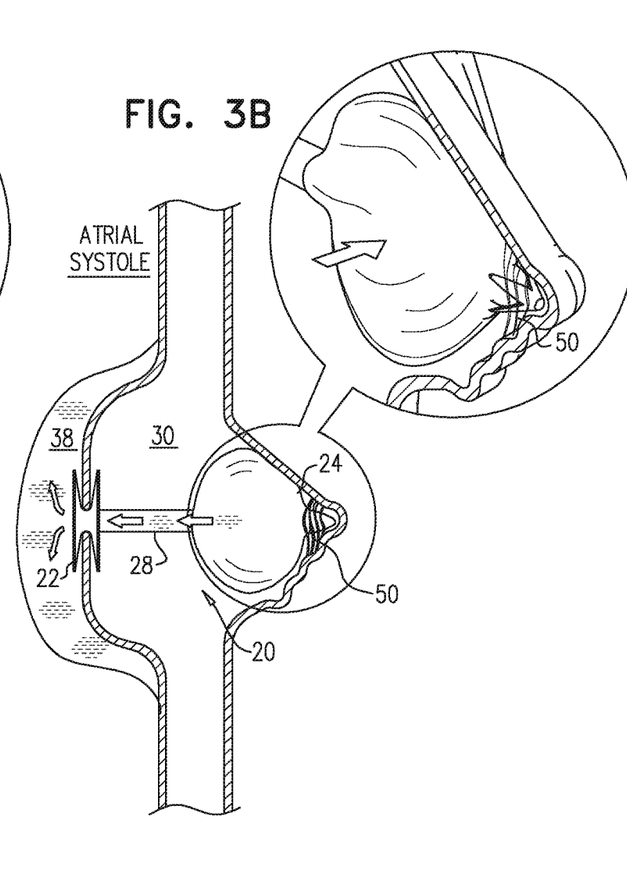

Reference is now made to FIGS. 3A-B, which show the operation of apparatus 20, in accordance with some applications of the present invention. During atrial diastole (FIG. 3A), blood is received from left atrium 38 into bag 24, via opening 26 in anchor 22 (and in some applications, also via shunt 28). (The flow of blood into the bag is passive, in that the pressure gradient between the two atria facilitates the flow.) As described hereinabove in the Summary, the reduced left atrial pressure, due to the flow of blood from the left atrium, helps relieve symptoms of left-side heart failure, e.g., by reducing congestion in the pulmonary vasculature. Then, during atrial systole (FIG. 3B), musculature of the right atrium, which may include musculature of right atrial appendage 40, is used to pump blood from the bag into the left atrium, by compressing the bag, e.g., while the bag is at least partly inside of the right atrial appendage. At least 2 cm3 and/or less than 8 cm3 (e.g., 3-5 cm3) of blood is pumped from the bag during atrial systole.

Figure 4A:
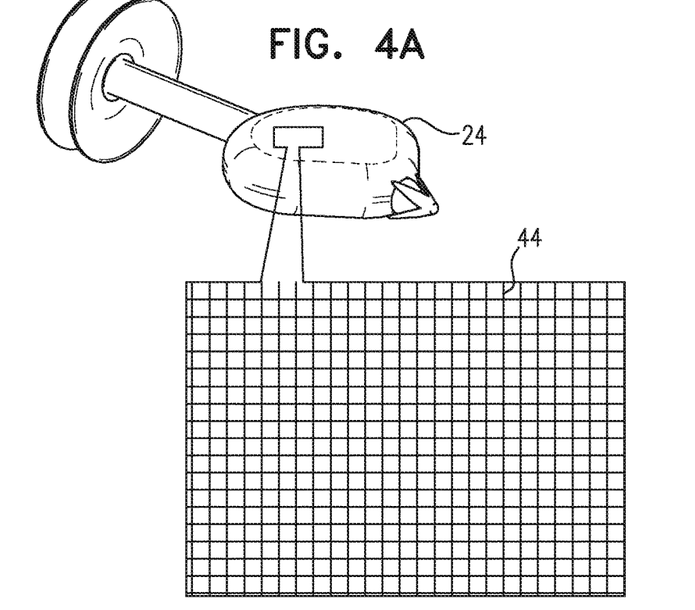
FIGS. 4A-B are schematic illustrations of an outer surface of a bag, in accordance with some applications of the present invention.
Figure 4B:
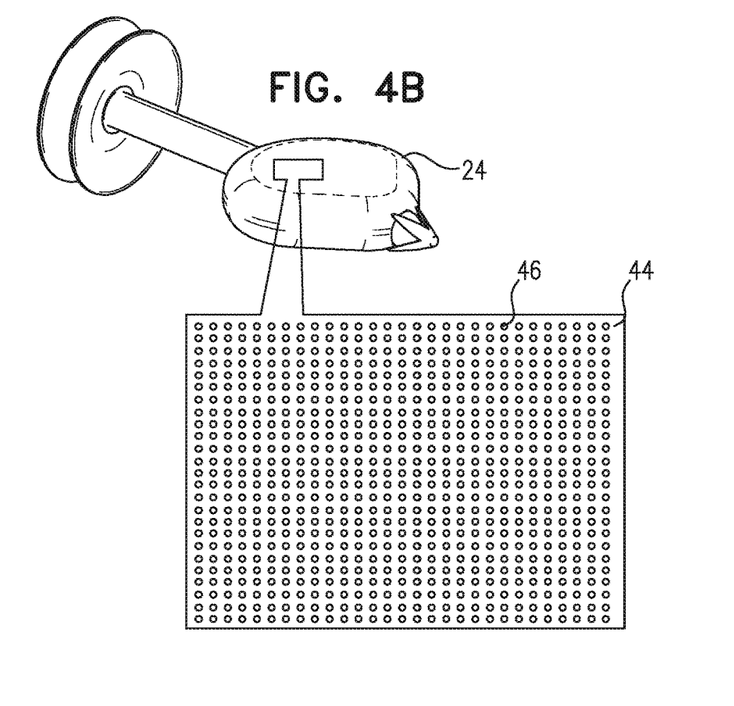

Reference is now made to FIGS. 4A-B, which are schematic illustrations of an outer surface 44 of bag 24, in accordance with some applications of the present invention. In some applications, to anchor the bag in the right atrium (e.g., in the right atrial appendage), fibrosis is induced, alternatively or additionally to using bag anchor 42. In such applications, outer surface 44 is typically rough, to facilitate the adherence of tissue to the bag. For example, as shown in FIG. 4A, the outer surface of the bag may be woven, e.g., it may comprise a woven mesh of fibers. Alternatively or additionally, as shown in FIG. 4B, the outer surface of the bag may be porous, e.g., it may be shaped to define a plurality of laser-drilled pores 46.

Figure 5A:
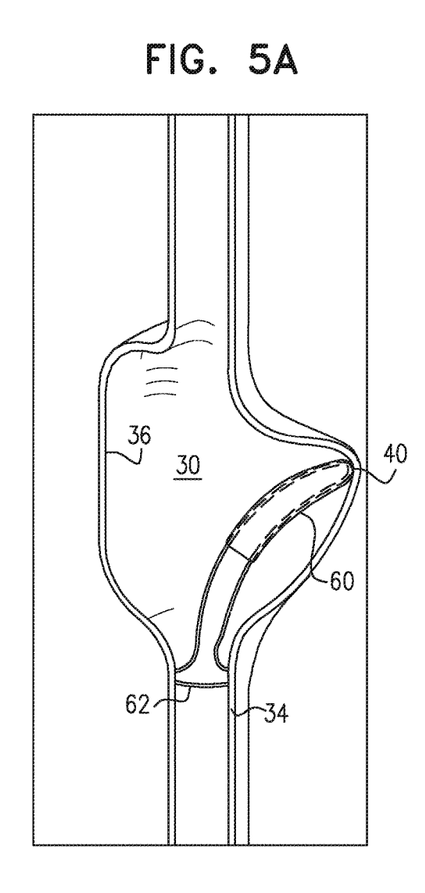
FIGS. 5A-B are schematic illustrations of a bag anchor and a bag, in accordance with some applications of the present invention.
Figure 5B:
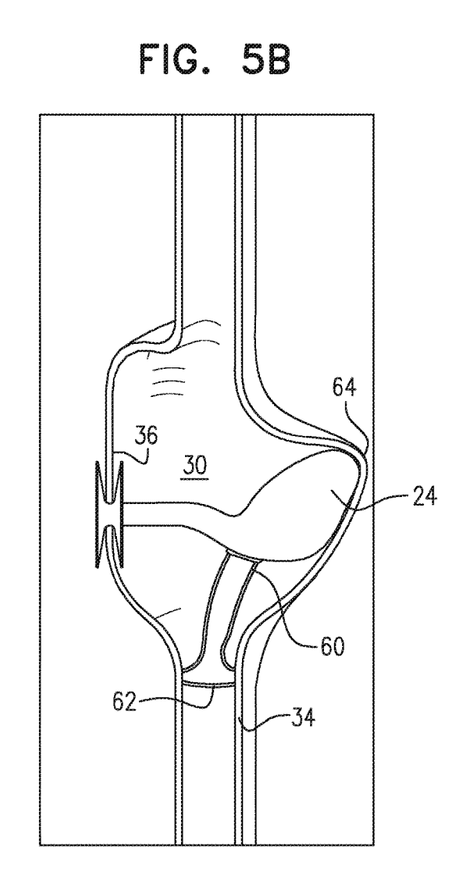

Reference is now made to FIGS. 5A and 5B, which are schematic illustrations of bag anchor 60 and bag 24 of apparatus 20, in accordance with some applications of the present invention. It is noted that FIG. 5A shows only the bag anchor in place in the subject's right atrium for illustrative purposes only. However, typically, bag 24 and bag anchor 60 are implanted at the same time as one another.

For some applications, bag anchor 60 is configured to form a structural bridge that spans from right atrial appendage 40 to the opposite side of right atrium 30 from the right atrial appendage. For example, as shown, at its proximal end (i.e., the end that is less advanced into the subject's right atrium), the anchor may define a loop 62 as shown. The loop is configured to become anchored to the wall of the right atrium around the inferior vena cava in the vicinity of the junction of the inferior vena cava and the right atrium, such that at least a portion of the loop is applying pressure to the wall of the right atrium on the opposite side of the right atrium from the right atrial appendage. As shown in FIG. 5B, the bag anchor is configured to hold bag 24 in place within the right atrium, and, typically, within the right atrial appendage. Typically, bag anchor 60 provides anchoring to the bag by pushing the bag toward outer wall 64 of the right atrium at the right atrial appendage. The anchor typically applies gentle pressure to the bag that is applied between the two ends of the anchor. For some applications, using an anchor as shown in FIGS. 5A-B reduces the risk of damage to the right atrial appendage relative to an anchor such as anchor 42 as shown in FIG. 1, which anchors the bag to tissue of the right atrial appendage, and does so over a relatively small area of the right atrial appendage.

As stated hereinabove, typically, bag 24 and bag anchor 60 are implanted at the same time as one another. For some applications, the bag and the bag anchor shown in FIG. 5A-B are implanted by first releasing the distal end of the anchor and the bag into the right atrial appendage, from an insertion device (such as catheter 32). Subsequently, the proximal end of the bag anchor (i.e., the end that defines loop 62) is released from the insertion device. Following the deployment of bag 24 and bag anchor 60, the interatrial septum 36 of the subject is punctured, and anchor 22 is subsequently anchored to interatrial septum 36, as shown in FIG. 2B, such that the anchor provides fluid communication between the left atrium 38 and bag 24. For some applications, the interatrial septum 36 of the subject is punctured and anchor 22 is anchored to interatrial septum 36, prior to the deployment of bag 24 and bag anchor 60.

Figures 6A, 6B:
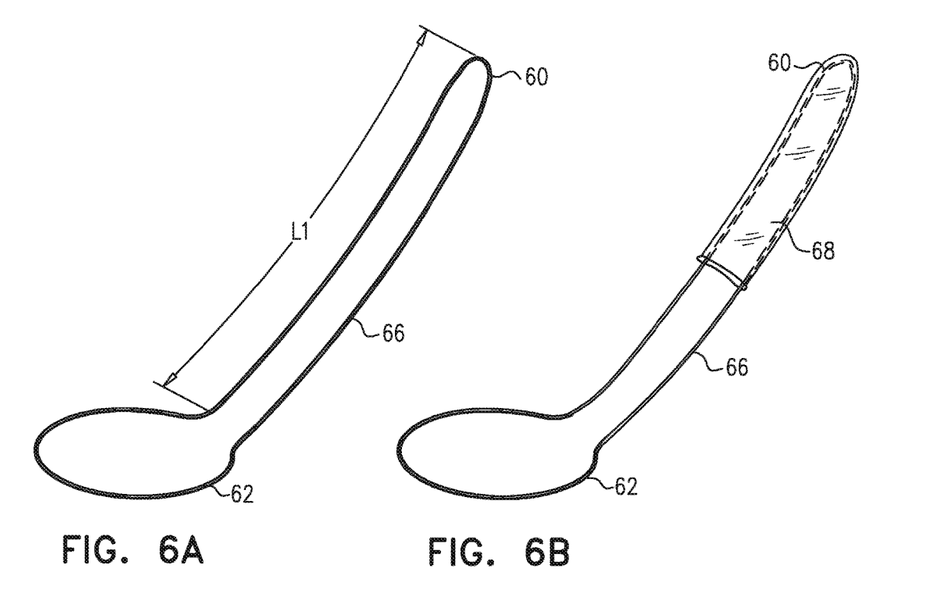
FIGS. 6A-B are schematic illustrations of a bag anchor, in accordance with some applications of the present invention.

Reference is now made to FIG. 6A-B, which are schematic illustrations of bag anchor 60, in accordance with some applications of the present invention. Typically, bag anchor 60 is made of a metal or an alloy, such as nitinol. For some applications, bag anchor 60 is shaped to define an elongate section 66, which is configured to span the right atrium, and loop 62, which is configured fit around the inferior vena cava in the vicinity of the junction of the inferior vena cava and the right atrium, as described above. Typically, elongate section 66 of the bag anchor has a length L1 of more than 4 cm (e.g., more than 5 cm), and/or less than 14 cm (e.g., less than 11 cm), e.g., 4-14 cm, or 5-11 cm. For some application, the diameter of loop 62 is more than 13 mm (e.g., more than 20 mm, or more than 25 mm), and/or less than 45 mm (e.g., less than 40 mm, or less than 35 mm), e.g., 13-45 mm, 20-40 mm, or 25-35 mm. For some applications, as show in FIG. 6B, the bag anchor defines additional structure 68 at the portion of the structure that directly contacts bag 24. For example, the anchor may define a metal surface, or may include a material (such as a solid piece of material, or webbed material) at the portion of the structure that directly contacts bag 24. Typically the structure provides additional support to bag 24.

Figure 6C:
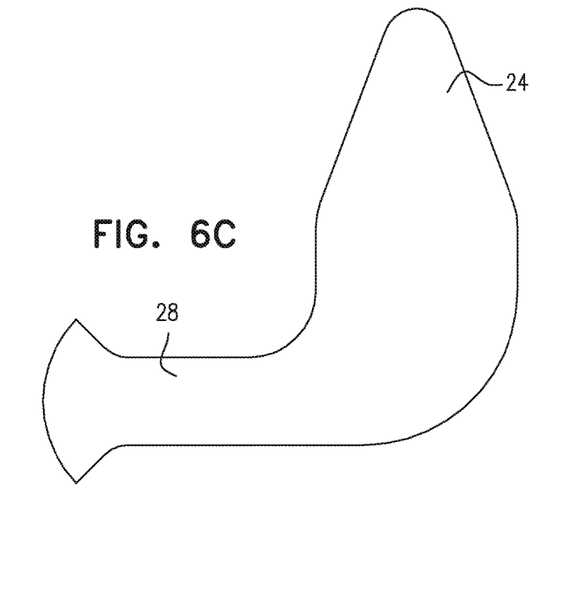
FIG. 6C is a schematic illustration two-dimensional illustration of a profile of a bag, in accordance with some applications of the present invention.

Reference is now made to FIG. 6C, which is a schematic illustration of a profile of bag 24, in accordance with some applications of the present invention. FIG. 6C is a two dimensional profile of bag 24, which is provided for illustrative purposes to show the shape of bag 24, in accordance with some applications of the present invention. For some applications, bag 24 defines a tear shape as shown in FIG. 6C, at least when the bag is fully expanded or fully flattened, in order to snugly fit into subject's right atrial appendage. For some applications, as shown shunt 28 is not a separate element from bag 24. Rather, for some applications, shunt 28 and bag 24 define a single integral structure, and/or are manufactured from a single continuous piece of material.

It is noted that, for illustrative purposes, the subject's anatomy is not drawn to scale in the present application. In addition, in some of the figures, the angle between the intra-atrial septum and the right atrial appendage is not shown accurately, for illustrative purposes, for example, in order to enhance other elements which are depicted in the figures. As noted hereinabove, and as indicated in FIG. 5B, apparatus 20 is typically not as straight as is shown in some of the figures; rather, bag 24 and/or shunt 28 typically turns, such that opening 26 is not aligned with the opposite end of the apparatus.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:
1. A method for treating a subject, the method comprising:
during atrial diastole of the subject, receiving blood from a left atrium of the subject into a bag that is disposed within a right atrium of the subject; and during atrial systole of the subject, utilizing musculature of the right atrium to pump blood from the bag into the left atrium, by compressing the bag.

2. The method according to claim 1, wherein utilizing musculature of the right atrium comprises utilizing musculature of a right atrial appendage of the subject.

3. The method according to claim 1, wherein compressing the bag comprises compressing the bag while the bag is at least partly inside of a right atrial appendage of the subject.

4. The method according to claim 1, wherein utilizing the musculature of the right atrium to pump the blood from the bag comprises utilizing the musculature of the right atrium to pump between two and eight cm3 of blood from the bag.

5. The method according to claim 4, wherein utilizing the musculature of the right atrium to pump the blood from the bag comprises utilizing the musculature of the right atrium to pump between three and five cm3 of blood from the bag.

6. A method comprising:
inserting an apparatus into a right atrium of a subject, the apparatus including an interatrial anchor and a bag in fluid communication with an opening of the anchor; and
anchoring the anchor to an interatrial septum of the subject, such that the anchor provides fluid communication between a left atrium of the subject and the bag.

7. The method according to claim 6, further comprising placing the bag in a right atrial appendage of the subject.

8. The method according to claim 6, further comprising using a bag anchor to anchor the bag to the right atrium of the subject.

9. The method according to claim 8, wherein anchoring the bag to the right atrium of the subject comprises anchoring the bag to a right atrial appendage of the subject.

10. The method according to claim 9, further comprising inducing fibrosis to anchor the bag to the right atrial appendage of the subject.

11. The method according to claim 6, wherein anchoring the bag to the right atrium of the subject comprises placing a structure in the right atrium that spans the right atrium from a right atrial appendage of the right atrium to an opposite side of the right atrium from the right atrial appendage.

12. The method according to claim 11, wherein placing the structure in the right atrium comprises placing a loop of the structure within the right atrium such that the loops around an inferior vena cava of the subject in a vicinity of a junction between the inferior vena cava and the subject's right atrium.

13. The method according to claim 11, wherein the structure defines an elongate section having a length that is between 4 cm and 14 cm.

14. The method according to claim 11, wherein anchoring the bag to the right atrium of the subject comprises pushing the bag toward an outer wall of the right atrium at the right atrial appendage, by placing the structure in the right atrium.

* * * * *